United States Patent
Minami

(10) Patent No.: US 6,758,807 B2
(45) Date of Patent: Jul. 6, 2004

(54) ELECTRONIC ENDOSCOPE WITH POWER SCALING FUNCTION

(75) Inventor: Itsuji Minami, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 133 days.

(21) Appl. No.: 10/226,253

(22) Filed: Aug. 23, 2002

(65) Prior Publication Data

US 2003/0050533 A1 Mar. 13, 2003

(30) Foreign Application Priority Data

Aug. 27, 2001 (JP) .......................................... 2001-255846
Sep. 28, 2001 (JP) .......................................... 2001-299228

(51) Int. Cl.[7] .............................................. A61B 1/05
(52) U.S. Cl. ........................ 600/168; 600/117; 348/240.1
(58) Field of Search .............................. 600/168, 167, 600/118, 117, 160, 109; 348/65, 71, 74, 76, 347, 240.1

(56) References Cited

U.S. PATENT DOCUMENTS 6,151,070 A * 11/2000 Sato et al. ............. 348/240.99
6,204,880 B1 * 3/2001 Nishimura ............. 348/240.99
6,348,948 B1 * 2/2002 Kyuma ........................ 348/360
6,396,538 B1 * 5/2002 Kobayashi et al. .... 348/240.99
6,425,858 B1 * 7/2002 Minami ...................... 600/168
6,508,760 B2 * 1/2003 Yamanaka et al. .......... 600/168
6,685,631 B2 * 2/2004 Minami ...................... 600/168
2001/0040630 A1 * 11/2001 Matsuzaka .................. 348/240

* cited by examiner

*Primary Examiner*—John P. Leubecker
(74) *Attorney, Agent, or Firm*—Snider & Associates; Ronald R. Snider

(57) ABSTRACT

An electronic endoscope equipped with an electronic zoom IC circuit that optically scales an object under observation using power scaling lenses and performs electronic power scaling processing on an image obtained by a CCD, wherein the electronic endoscope sets a predetermined depth of field by driving the power scaling lenses with the image optically magnified based on an operation of a variable depth switch and maintains the magnification immediately before this switch operation through electronic power scaling processing. This makes it possible to change a depth of field and observe an image magnified under an equal magnification focused in the depth direction on the monitor. The electronic endoscope can also form a plurality of still images of different depths of field based on an operation of the freeze switch and record optimal still images.

8 Claims, 9 Drawing Sheets

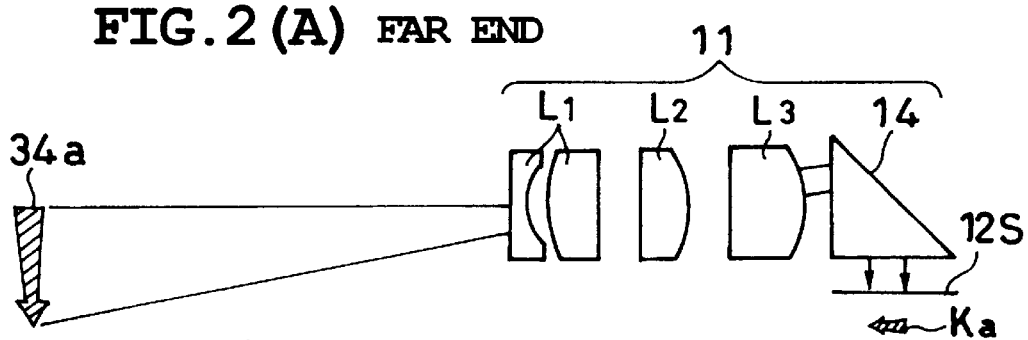
FIG. 2(A) FAR END
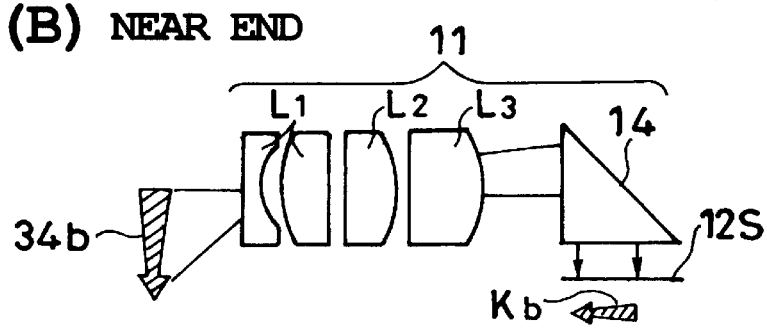
FIG. 2(B) NEAR END
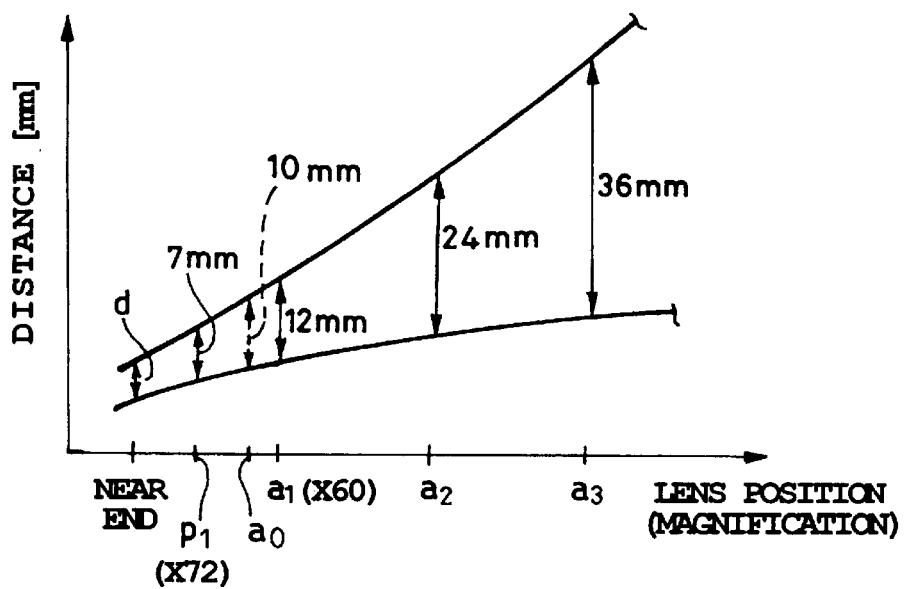
FIG. 3

[FUNCTION SETTING]

ELECTRONIC ENDOSCOPE WITH POWER SCALING FUNCTION

BACKGROUND OF THE INVENTION

This application claims the priority of Japanese Patent Applications Nos. 2001-255846 filed on Aug. 27, 2001 and 2001-299228 filed on Sep. 28, 2001, which are incorporated herein by reference.

1. Field of the Invention

The present invention relates to an electronic endoscope with a power scaling function and, more particularly, to power scaling operation control of an electronic endoscope capable of observing an optically magnified image by a movable lens and forming an electronically magnified image through signal processing.

2. Description of the Related Art

An electronic endoscope, etc. in recent years has an objective lens system at the tip of its scope provided with a power scaling movable lens and drives this movable lens using an actuator, etc. to optically magnify an image of an object under observation. This optically enlarged image is picked up by an image pick-up element such as a CCD (Charge Coupled Device), and various types of image processing are performed by a processor based on the output signal from the CCD, by which an enlarged image of a subject to be observed is displayed on a monitor. In such an optical variable power mechanism, an observed image can be enlarged up to about 70 to 100 times.

On the other hand, conventionally, the image obtained by the CCD is enlarged electronically by picture element interpolation processing etc. of an electronic variable power circuit. According to this, the optically enlarged image can be further enlarged and displayed on the monitor for observation.

The power scaling function of such an electronic endoscope electronically magnifies an image which has been optically magnified under an arbitrary magnification using optical power scaling and electronic power scaling switches respectively or operates by associating optical power scaling with electronic power scaling using a common power scaling switch of an endoscope operation section. When this common power scaling switch is used, the movable lens is moved to the magnification end (near end) by optical power scaling, and then optical power scaling is automatically changed to electronic power scaling to form a further magnified image through signal processing, which makes it possible to observe specific areas such as affected areas speedily and under an optimal magnification.

SUMMARY OF THE INVENTION

However, the optical power scaling mechanism using a movable lens in the above-described conventional electronic endoscope has a smaller depth of field as the magnification increases and there are cases where the electronic endoscope cannot optimally display an overall image of an object under observation with an uneven surface in the depth direction. This phenomenon will be described now with reference to FIGS. 12 and 13.

In FIG. 12, the left-hand side view shows a state in which when a movable lens 1 lies at the Far end, the proximal end, a subject to be observed 2 forms an image on a CCD image pick-up surface 3, and the right-hand side view shows an image formation state at the time when the moving lens 1 is moved to the Near side, the enlargement side. In FIG. 12, since the moving lens 1 is set at a position of distance 0, at the time of enlargement, the image pick-up surface 3 is drawn so as to be shifted rearward. Actually, the moving lens 1 moves forward. When the optical enlargement is not made as shown in the left-hand side view of FIG. 12, the focus is sharpened, for example, at a distance of 8 to 100 mm, and the depth of field is 92 mm. Whereas, when the optical enlargement is made as shown in the right-hand side view in FIG. 12, the focus is sharpened at a distance of 4 to 20 mm, and the depth of field is 16 mm.

FIG. 13 is an explanatory view of the depth of field. Taking the focal length of a lens 4 as f, the F number as $F_N$, the allowable blur circle as $\delta$, and the distance of subject to be observed as L, the rear depth of field $L_r$ and the front depth of field $L_f$ are expressed as follows:

$$L_r = (\delta \cdot F_N \cdot L^2)/(f^2 - \delta \cdot F_N \cdot L) \tag{1}$$

$$L_f = (\delta \cdot F_N \cdot L^2)/(f^2 + \delta \cdot F_N \cdot L) \tag{2}$$

The depth of field of this lens 4 is a value obtained by summing up the rear depth of field $L_r$ and the front depth of field $L_f$, that is, $L_r + L_f$. The depth of focus is $2\delta \cdot F_N$.

The aforementioned depth of field explained in FIG. 12 is also the above-described value of $L_r + L_f$, and the range in which the focus is sharp is 92 mm at the Far end and 16 mm at the Near end. In the configuration of variable power objective optical system now used for an endoscope, the depth of field decreases as the image is enlarged. Therefore, in the case where a subject to be observed having irregularities is observed, the depth of field becomes shallow (short), so that a blur occurs somewhere in the depth direction. When the subject to be observed caught in a state of shallow depth of field is enlarged electronically, the blur in the depth direction is also enlarged, which presents a problem in that the whole of the subject to be observed cannot be displayed and observed with high picture quality.

The present invention has been implemented in view of the above-described problem and it is an object of the present invention to provide an electronic endoscope having a power scaling function capable of eliminating blurring in the depth direction by switching only the depth of field to an optimal value and smoothly observing an image.

To attain the above-described object, the present invention is characterized by including an objective optical system that optically scales power of an image under observation using a power scaling lens, an electronic power scaling circuit that electronically scales the image obtained through an image pickup element through signal processing, depth operating means that changes the depth of field at the optical power scaling to an arbitrary value and a control circuit that drives and controls the objective optical system so that the objective optical system is set to the depth of field selected by the operation of this depth operating means and controls the electronic power scaling operation of the electronic power scaling circuit so that it maintains the magnification of the image immediately before the depth operation.

Since the depth of field is specified by the position of the movable lens to magnify the image, the depth of field can also be recognized by the optical magnification. According to the above-described configuration, assuming that a predetermined depth of field (e.g., depth equivalent to ×60) is selected by the depth operating means when an image is magnified to ×72, for example, through optical power scaling, ×1.2 is set by electronic power scaling. This makes it possible to display a magnified image under the same magnification as that immediately before the depth operation. Furthermore, assuming that the depth of field value is 7 mm under ×72 and 12 mm under ×60 as described above, it is possible to widen the sharply focused range 5 mm in the depth direction and observe a magnified image focused within a desired range.

Furthermore, the control circuit can be controlled so that it does not electronically scale power beyond a preset allowable magnification range when the depth of field is changed to an arbitrary value.

The depth operating means can be constructed by including a selection switch that selects a plurality of preset depth of field values and a variable switch to change the depth of field values selectable by this switch. Furthermore, this depth operating means can also be made to increase the depth of field from the immediately preceding value by a predetermined amount when a depth of field change operation is performed.

Another embodiment of the present invention is characterized by including an objective optical system that optically scales an image under observation using a power scaling lens, an electronic power scaling circuit that electronically scales the image obtained through an image pickup element through signal processing, depth operating means that presets a comparative observation depth of the depth of field which changes through the optical power scaling operation and a control circuit that drives and controls, when a predetermined operation is performed during execution of optical power scaling, the objective optical system so that the objective optical system is set to the comparative observation depth set by the depth setting means and controls the electronic power scaling operation of the electronic power scaling circuit so that the magnification of the image with the comparative observation depth taken by the image pickup element is identical to the magnification immediately before the depth operation.

In the above-described embodiment, assuming that the predetermined operation is an operation of displaying a still image of a freeze switch, it is possible to simultaneously display the still image during an operation of the freeze switch and the still image of the comparative observation depth on a partitioned screen on the monitor.

According to the above-described other embodiment, the depth setting means can preset, for example, three (one or a plurality of) comparative observation depths and when a predetermined operation member (e.g., the freeze switch) is turned ON while optical power scaling is set to a magnification of ×A, for example, a ×A image is displayed on one small screen of the 4-partitioned screen and at the same time, three images obtained by setting the power scaling movable lenses to three comparative observation depths one by one are displayed on the rest of the small screens of the 4-partitioned screen under the same magnification ×A. That is, when the depth of field changes, the optical magnification also changes, and therefore compensating for this change by electronic magnification processing allows an image to be formed under the same magnification.

For example, suppose the depth setting means has set comparative observation depths of 12 mm, 24 mm and 36 mm. These depths can be specified at the drive positions of the movable lens and also recognized by the power of optical magnification and the comparative observation depths are equivalent to ×60, ×50 and ×40 in that order. Assuming that the magnification ×A is ×56, the power of electronic power scaling is set to approximately ×0.933 for an image with a depth of field of 12 mm, ×1.12 for an image of 24 mm, and ×1.4 for an image of 36 mm. As a result, it is possible to display four magnified images with different focused depth ranges under the same magnification.

BRIEF DESCRIPTION OF THE DRAWINGS

FIG. 2A illustrates a configuration of an objective optical system according to the embodiment and how an image is formed at the Far end;

FIG. 2B illustrates a configuration of the objective optical system according to the embodiment and how an image is formed at the Near end;

FIG. 3 illustrates a depth of field and lens position set by the objective optical system according to the first embodiment;

DETAILED DESCRIPTION OF THE PREFERRED EMBODIMENTS

First Embodiment

Figure 1:
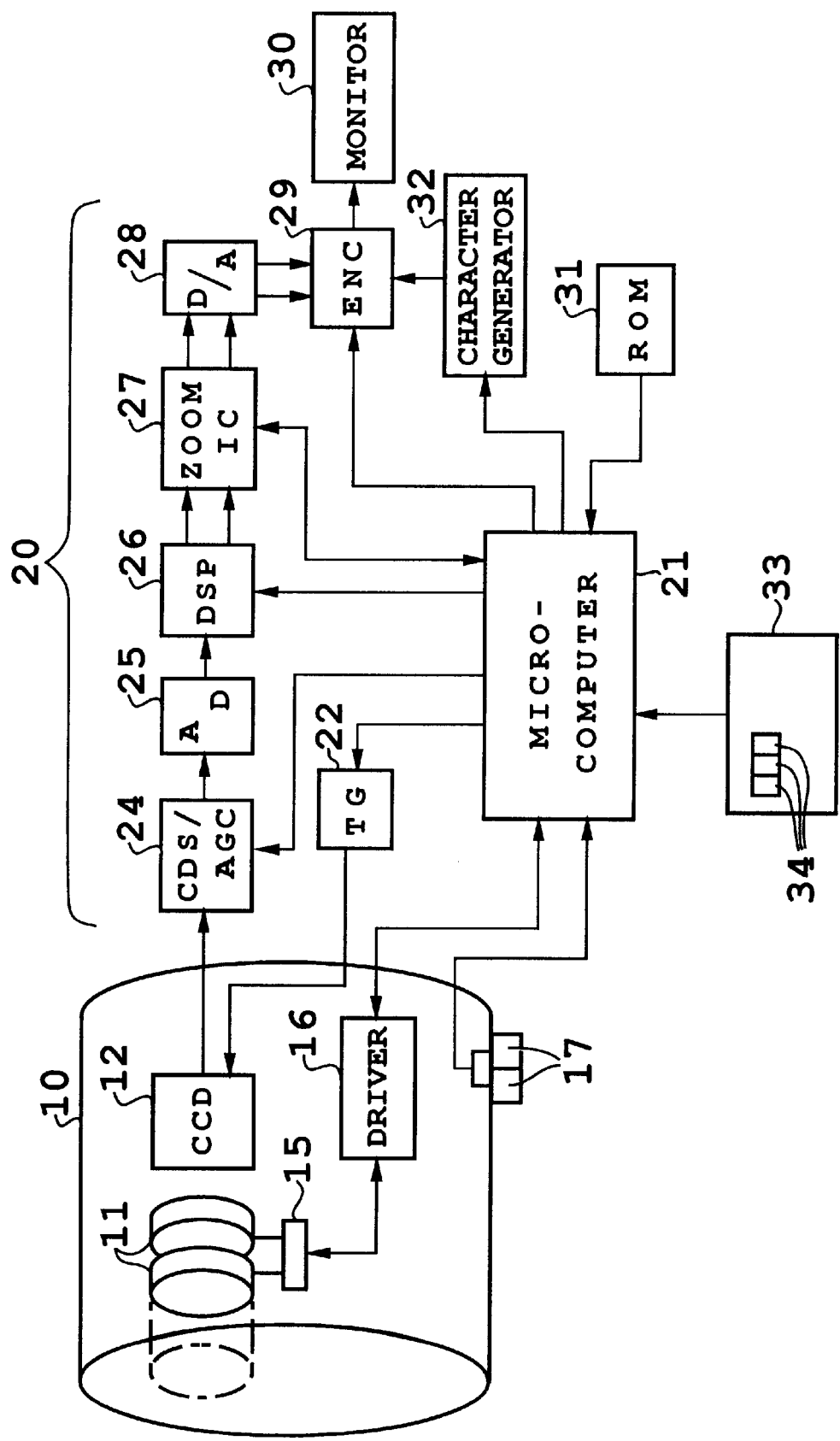
FIG. 1 is a block diagram showing a configuration of an electronic endoscope according to a first embodiment of the present invention.

FIG. 1 shows a configuration of an electronic endoscope according to a first embodiment. In FIG. 1, an objective optical system 11 with power scaling lenses is provided at one end of an electronic scope (electronic endoscope) 10 and a CCD 12 is placed in such a way that its image pickup plane coincides with the image forming position of this objective optical system 11. The objective optical system 11 has a configuration as shown in FIGS. 2A and 2B, for example.

As shown in FIGS. 2A and 2B, the objective optical system 11 is constructed of a fixed first lens (group) $L_1$, a movable second lens $L_2$ which mainly has a power scaling function and a movable third lens (group) $L_3$ which has other functions (e.g., to change a curvature characteristic of an image surface) and an image pickup surface 12S of the CCD 12 is placed behind this third lens $L_3$ via a prism 14. According to the objective optical system 11, relatively moving the second lens $L_2$ and third lens $L_3$ in the optical axis direction makes it possible to scale power of the image and change a curvature characteristic of the image surface, for example. In this embodiment, moving both the second lens $L_2$ and third lens $L_3$ forward magnifies the image.

In FIG. 1, an actuator and position detector 15 is provided which drives the second lens $L_2$ and third lens $L_3$ of the objective optical system 11 and as this actuator, a linear actuator or an actuator constructed in such a way as to rotate and drive a linear transmission member by a motor, convert this rotational movement to linear movement to drive the lenses $L_2$ and $L_3$. This actuator and position detector 15 is provided with a driver 16 to keep track of the lens position and execute a power scaling operation.

Furthermore, the operation section, etc. of the electronic scope 10 is provided with a power scaling switch (2-action switch) 17 which operates the Near (magnifying) direction and Far (reducing) direction for both optical magnification and electronic magnification. That is, this power scaling switch 17 (depth of field preferential mode) performs optical magnification first, and after moving the second lens $L_2$ to the magnification end (Near end), it automatically changes to electronic magnification.

On the other hand, in the processor 20, there are a microcomputer 21 that controls the actuator driver 16, inputs an operation signal for the power scaling switch 17 to perform various types of control such as optical power scaling and electronic power scaling, and performs control to form an equal-magnification image of the depth of field selected based on an operation of a variable depth equal-magnification observation switch (34) which will be described in detail later and a timing generator (TG) 22 that supplies a control signal to read an image pickup signal to the CCD 12.

As a video signal processing system, there are a CDS (correlation double sampling)/AGC (automatic gain control) circuit 24, an A/D converter 25, a DSP (Digital Signal Processor) 26 that performs various types of digital processing such as white balance, gamma correction, contour correction, an electronic zoom IC circuit 27 which is an electronic power scaling circuit, a D/A converter 28 and an encoder (ENC) 29 which performs output processing according to the monitor type, and the output of this encoder 29 is supplied to a monitor 30. The electronic zoom IC circuit 27 stores a video signal captured by the DSP 26 in memory and can form a magnified image through processing such as interpolating elements in the horizontal and vertical directions.

The processor 20 is further provided with a ROM (read only memory) 31 that stores values such as the depth of field and magnification, data to form other characters or operation data, etc. to calculate the position of the variable lens $L_2$ (or $L_3$) corresponding to the depth of field and a character generator 32 to generate various characters, and this character generator 32 forms character images such as the depth of field during a power scaling operation and magnification to be displayed on the monitor 30.

On an operation panel 33 of the processor 20 are various keys and, for example, three (or any number of) variable depth equal-magnification observation switches 34, which make it possible to select three depths of fields. The depth of field values selectable by these variable depth equal-magnification observation switches 34 in this first embodiment can be set to an arbitrary value by displaying a function setting screen on the monitor 30 beforehand and entering values using various keys. These variable depth equal-magnification observation switches 34 can also be placed on the electronic scope 10 side.

Then, the microcomputer 21 stores the position of the second lens $L_2$ corresponding to the depth of field set by the variable depth equal-magnification observation switches 34 in an internal storage section (RAM, etc.). As shown in FIG. 3, assuming that, for example, 12 mm, 24 mm and 36 mm are set as the depth of field values in this embodiment, the lens positions $a_1$, $a_2$ and $a_3$ which correspond to the depths of field are stored.

When a depth of field signal is input through an operation of the variable depth equal-magnification observation switches 34 during an arbitrary magnification operation, this microcomputer 21 calculates an electronic power scaling magnification Ce from the lens position ($a_1$, $a_2$, $a_3$) corresponding to this depth of field signal and the current position p of the second lens $L_2$. For example, assuming that the magnification (Ca) of the lens position $a_1$ (focal distance $f_1$) is ×60 and the magnification (Cp) of the currently driven lens position $p_1$ (focal distance $f_2$) is ×72, Ce=Cp/Ca=72/60=1.2 is calculated. Then, the microcomputer 21 controls the electronic zoom IC circuit 27 so that it performs electronic magnification under the electronic magnification Ce and thereby forms an image at the same magnification as immediately before the operation of the switch 34.

The first embodiment is configured as shown above, and its action will be explained below. In this apparatus, when the power scaling switch 17 of the electronic scope 10 is operated, the second lens $L_2$ (and third lens $L_3$) is moved and controlled by the driver 16 and actuator 15, a magnified image is obtained from a basic image by focusing in the Near direction and a reduced image is obtained by focusing in the Far direction in the direction returning to the basic image and these images are taken by CCD 12.

That is, when the power scaling switch 17 is not operated, the variable second lens $L_2$ (and $L_3$) is placed to the Far end, and as shown in FIG. 2A, an image of an object 34a at a far distance is formed as an image Ka on the image pickup plane 12S, and when a magnifying operation is performed using the power scaling switch 17, as shown in FIG. 2B, the movable second lens $L_2$ moves forward and an image of the object 34b at a short distance is formed as an image Kb at the time of maximum magnification (Near end).

The signal output from the CCD 12 is read by a read signal of the timing generator 22, subjected to correlation double sampling and amplification processing by the CDS/AGC circuit 24 and subjected to various kinds of processing by the DSP 26 as a digital signal. A video signal formed in this way is output through the electronic zoom IC circuit 27, encoder 29 to the monitor 30, and when the optical power scaling is performed as shown above, the optically magnified object image is displayed on the monitor 30. When a magnifying operation of the power scaling switch 17 is performed, electronic magnification processing is performed by the electronic zoom IC circuit 27 in the same lens position (Near end) in FIG. 2B and the further optically magnified image of the object is displayed on the monitor 30.

Figure 4:
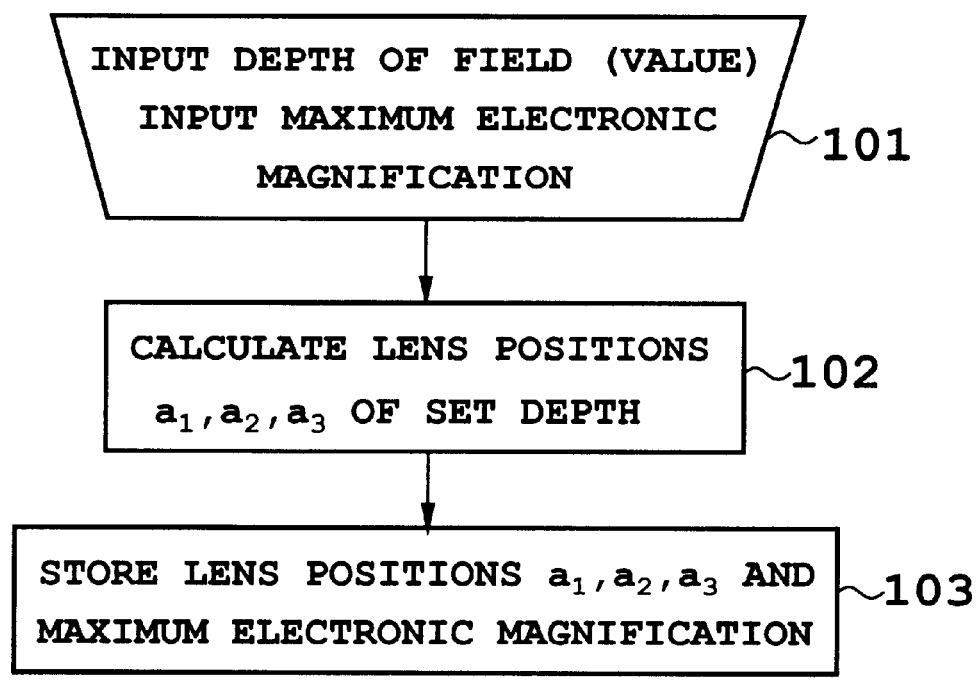
FIG. 4 is a flow chart showing an operation of setting the depth of field of a variable depth equal-magnification observation switch of the embodiment.

On the other hand, this apparatus can select/set a depth of field to an arbitrary value using the variable depth equal-magnification observation switches 34 and the setting of the depth of field for that purpose is performed through the operation in FIG. 4. That is, in step 101 in FIG. 4, when three depth of field values (12 mm, 24 mm, 36 mm in FIG. 3) are input from the keys, etc. on the operation panel 33 on the function setting mode screen, etc. displayed on the monitor 30, the positions $a_1$, $a_2$ and $a_3$ of the movable lens $L_2$ corresponding to this depth of field are calculated in step 102 and these lens positions are stored/retained in memory, etc. as the selected/set values of the variable depth equal-magnification observation switches 34 in step 103. Furthermore, this embodiment is designed to enter a maximum magnification b (e.g., ×2 to ×3) of allowable electronic magnification and this magnification value is also stored/set.

Figure 5:
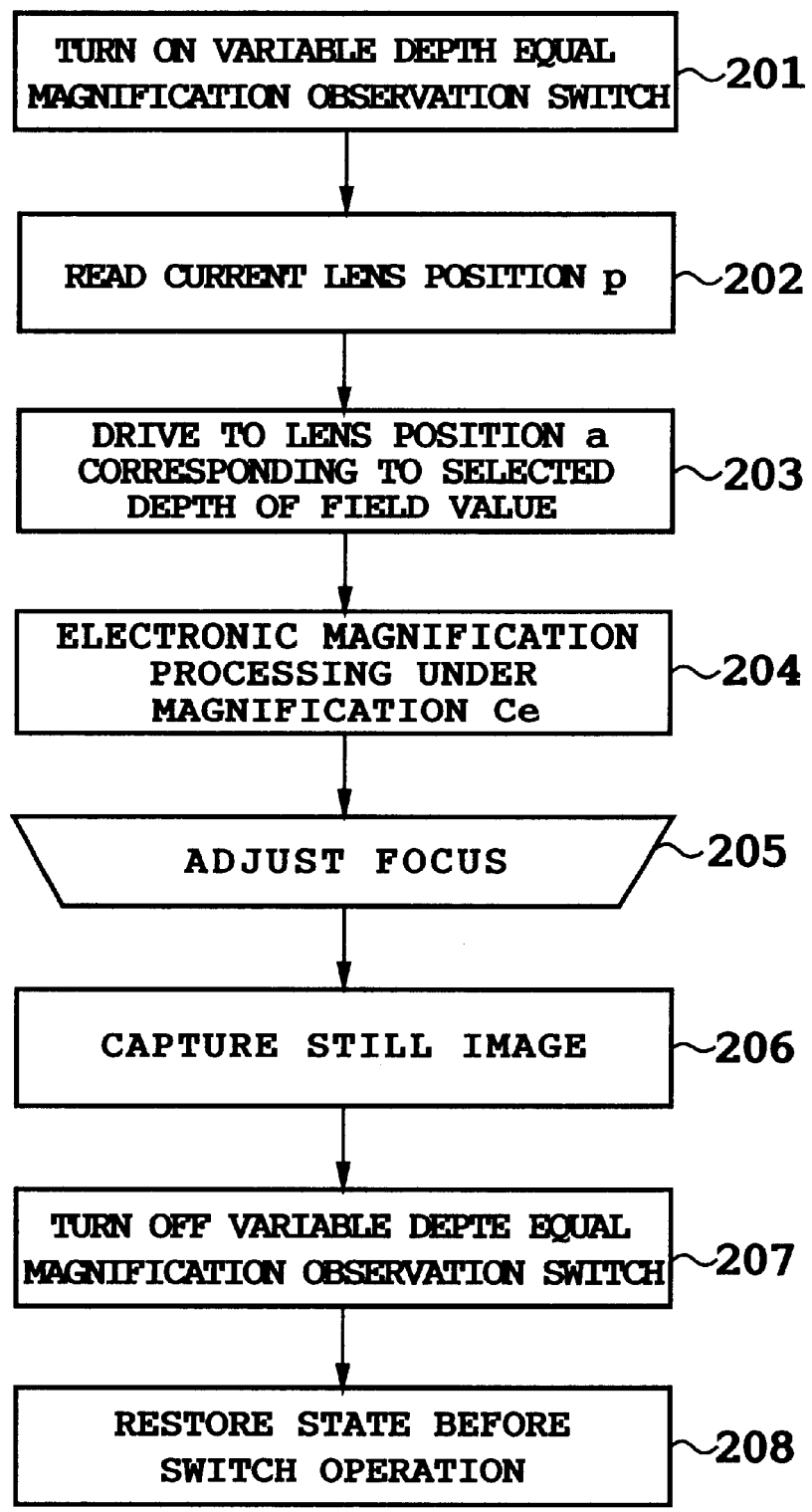
FIG. 5 is a flow chart showing an overall operation based on the variable depth equal-magnification observation switch of the first embodiment.

FIG. 5 shows an overall operation carried out based on the operation of the variable depth equal-magnification observation switches 34 (mainly operations related to the microcomputer 21) and when the variable depth equal-magnification observation switches 34 are turned ON in step 201, the current position p of the second lens $L_2$ is read in step 202 and the driver 16 drives the movable lens $L_2$ from the current position to the lens position of the selected depth of field in next step 203. For example, if the selected depth of field is 12 mm, the lens is moved to the lens position of $a_1$ as shown in FIG. 3.

Then, in step 204, a magnification Ce of electronic power scaling is calculated from the lens position $a_1$ of this selected depth of field and current position p of the second lens $L_2$ and electronic power scaling under this magnification Ce is controlled. That is, as shown in FIG. 3, assuming that the lens position corresponding to the depth of field of 12 mm is $a_1$ (optical magnification Ca=×60) and the current position of the second lens $L_2$ is $P_1$ (depth of field 7 mm, optical magnification Cp=×72), the magnification Ce of electronic power scaling is Cp/Ca=72/60=1.2 as shown above. Therefore, the electronic zoom IC circuit 27 in FIG. 1 carries out ×1.2 electronic magnification processing, and as a result, a ×72 magnified image which is the same magnification as that of the immediately preceding operation is formed and a magnified image with the depth of field changed from 7 mm to 12 mm is displayed on the monitor 30.

Then, in next step 205, the user of the endoscope adjusts the focus if necessary. That is, changing the depth of field by moving the movable lens $L_1$ widens the sharply focused range, and therefore the focus needs to be adjusted within a desired range in the depth direction through fine adjustment of the position of the end of the endoscope. Then, in step 206, a still image capturing operation is performed and when the desired magnified image is obtained, a still image is formed from the current magnified moving image based on the operation of the still image recording switch, etc. provided in the electronic scope 10 and this is recorded in a recording apparatus such as a hard copy.

Then, in step 207, when the variable depth equal-magnification observation switches 34 are turned OFF, processing for restoring the original condition before the switch operation is performed in step 208. That is, the second lens $L_2$ is returned to the position of $p_1$ and the electronic magnification is set to ×1 (electronic magnification processing by the electronic zoom IC circuit 27 is stopped). By the way, the second lens $L_2$ is at the Near end and electronic magnification has already been executed immediately before the variable depth equal-magnification observation switches 34 are operated, and in this case, the electronic magnification immediately before the switch operation is restored.

By operating the variable depth equal-magnification observation switches 34 during a magnification operation makes it possible to obtain an image of the same magnification as the image before the operation of the switch 34 with a selected arbitrary depth of field of not only 12 mm but also 24 mm and 36 mm in this first embodiment. In this embodiment, a maximum value of electronic magnification is set to a predetermined value (×2, ×3), and even if the calculated value Ce is greater than this value, the image will not be magnified more than the predetermined value and in this way blurring of the image by electronic magnification is prevented.

Furthermore, the first embodiment adopts a depth of field preferential mode in which the power scaling switch 14 operates optical power scaling in association with electronic power scaling and the depth of field value for switching from optical power scaling to electronic power scaling can be set to an arbitrary value. That is, it is normally possible to switch to electronic power scaling with the depth of field value (d) at the Near end shown in FIG. 3, but it is possible to execute a depth of field preferential mode that allows this switching depth of field to be set to an arbitrary value which is deeper than d. For example, assuming that the switching depth of field in the depth of field preferential mode is set to 10 mm as shown in FIG. 3, optical power scaling is switched to electronic power scaling when the second lens $L_2$ is moved to position $a_0$.

In the first embodiment, three depth of field values can be set for the variable depth equal-magnification observation switches 34, but it is also possible to provide a depth value variable switch, etc. together with one variable depth equal-magnification observation switch 34 to freely make variable the depth of field to be operated by the variable depth equal-magnification observation switch 34. Furthermore, when the depth of field immediately before the operation of this variable depth equal-magnification observation switch 34 is deeper than the value set by the switch 34, it is also possible to invalidate the operation of the switch 34. Furthermore, it is also possible to control so that a shift is made in the direction in which the depth of field (lens position) becomes deeper by a predetermined uniform amount when this variable depth equal-magnification observation switch 34 is operated irrespective of the magnification under which the switch is operated.

As explained above, the first embodiment provides a depth of field operating means for changing the depth of field to an arbitrary value for optical power scaling, drives and controls the objective optical system so that the depth of field selected by the operation of this depth operating means is obtained and controls the electronic power scaling operation of the electronic power scaling circuit so that the magnification of the image immediately before the operation is maintained, and can thereby eliminate blurring in the depth direction by switching only the depth of field to an optimal value during an observation of a magnified image and smoothen the observation of the image by the electronic endoscope having a power scaling function.

Second Embodiment

Figure 6:
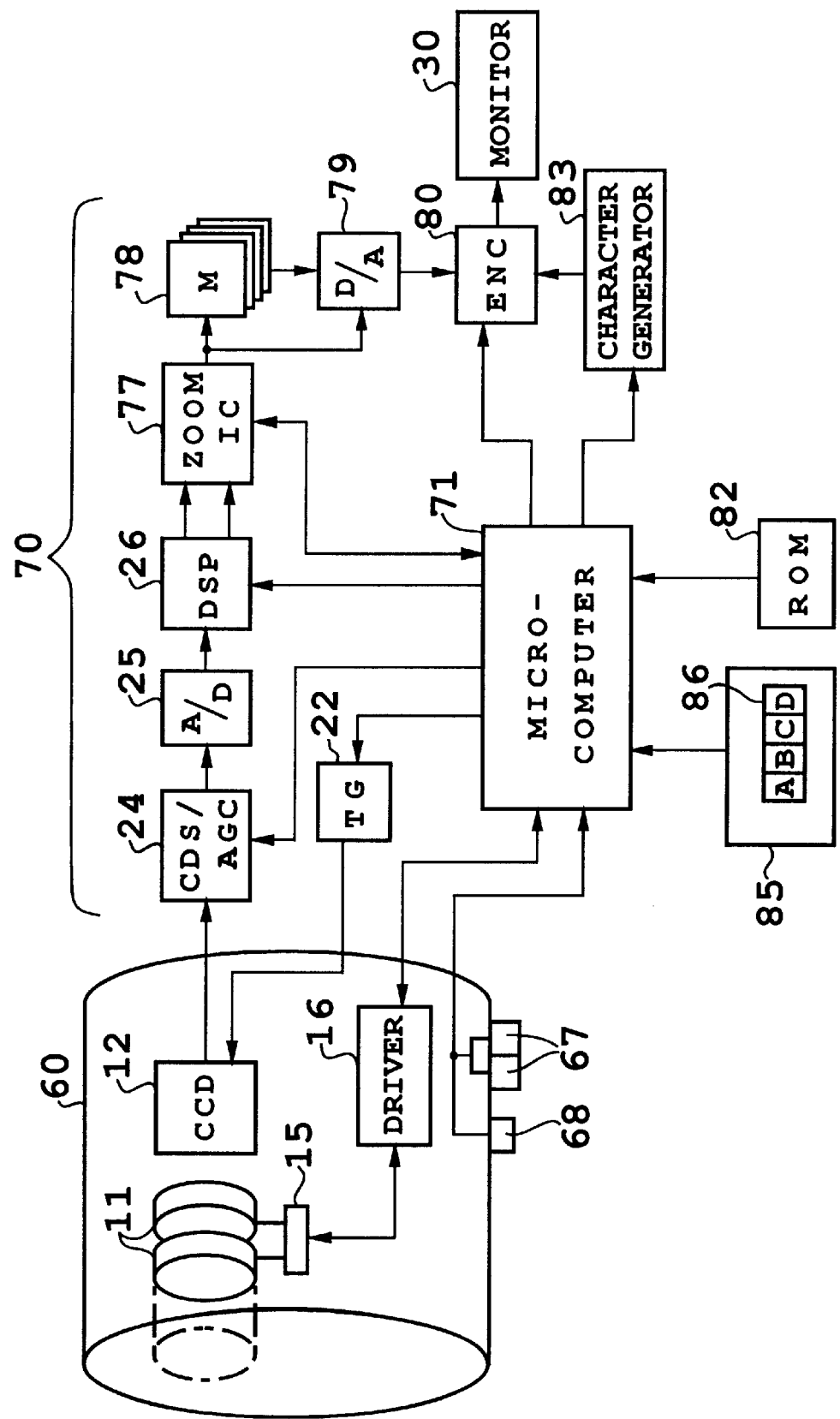
FIG. 6 is a block diagram showing a configuration of an electronic endoscope according to a second embodiment of the present invention.

FIG. 6 shows a configuration of an electronic endoscope according to a second embodiment and its basic configuration is the same as that of the first embodiment. As shown in FIG. 6, an objective optical system 11 with power scaling lenses configured as shown in FIG. 2 and a CCD 12 are provided at the end of an electronic scope 60 and an actuator 15 and a driver 16 are provided to drive movable lenses in the objective optical system 11.

Furthermore, the operation section of the electronic scope 60 is provided with a power scaling switch 67 which operates both optical magnification and electronic magnification, for example, and freeze switch 68, etc. That is, this power scaling switch 67 also performs optical magnification first, and after moving the second lens $L_2$ from base end (Far end) to the magnification end (Near end), it changes to electronic magnification. Furthermore the freeze switch 68 consists of a two-stage switch so that an operation of the first stage forms a still image and an operation of the second stage outputs a recording trigger to the recording apparatus.

On the other hand, in the processor 70, there are a microcomputer 71 that controls the actuator driver 16, inputs an operation signal for the power scaling switch 67 to perform various types of control such as optical power scaling and electronic power scaling, and performs control displaying of four still images with different depths of field on four screens and a timing generator (TG) 22.

Furthermore, there are a CDS (correlation double sampling)/AGC (automatic gain control) circuit 24, an A/D converter 25, a DSP 26 that performs various types of digital processing, an electronic zoom IC circuit 77 which is an electronic power scaling circuit, image memories 78 that store four still images, a D/A converter 79 and an encoder (ENC) 80, and the output of this encoder 80 is supplied to a monitor 30.

The processor 70 is further provided with a ROM 82 that stores data to calculate the position of the movable lens $L_2$ corresponding to the depth of field and a character generator 83, and this character generator 83 forms character images such as the depth of field during a power scaling operation and magnification to be displayed on the monitor 30.

Figure 7:
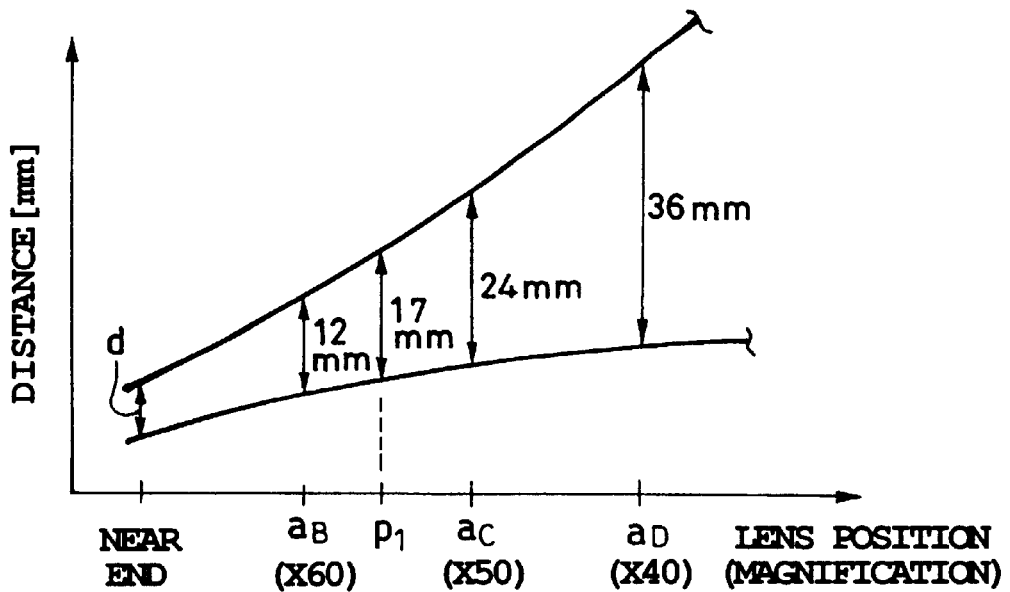
FIG. 7 illustrates a depth of field and lens position set by the objective optical system according to the second embodiment.

On an operation panel 85 of the processor 70 are various keys and, for example, four image selection switches 86 of A, B, C and D and one image is selected from the 4 partitioned screens on the monitor 30 by this image selection switch 86. This operation panel 85 allows the user to preset a comparative observation depth of field value of a still image selectable by the image selection switch 86 while watching the screen of the monitor 30. FIG. 7 shows a relationship between a depth of field (d) and lens position and this image selection switch 86 makes it possible to set, for example, lens positions $a_B$, $a_C$ and $a_D$ and comparative observation depths of field 12 mm, 24 mm and 36 mm, etc.

Then, a microcomputer 71 in the second embodiment executes processing of a still image 4-partitioned screen display when the first stage of the freeze switch 68 is pressed during an execution of optical magnification by the power scaling switch 67 and outputs the selected still image to the recording apparatus such as a hard copy, filing apparatus when the second stage of the freeze switch 68 is pressed after one of the 4 partitioned screens displayed on the monitor 30 is selected by the image selection switch 86. Furthermore, when the second stage of the freeze switch 68 is pressed without selecting the above-described image, the microcomputer 71 controls so that all the four screens are output to the recording apparatus.

Furthermore, when the first stage of the freeze switch 68 is pressed during an optical magnification operation, this microcomputer 71 calculates magnifications $C_B$, $C_C$ and $C_D$ of electronic power scaling so that the above-described three comparative observation depth images have the same magnification as that of the original image immediately before the operation of the freeze switch 68. For example, as shown in FIG. 7, assuming that the magnifications at the lens position $a_B$ (focal distance $f_1$), lens position $a_C$ (focal distance $f_2$) and lens position $a_D$ (focal distance $f_3$) correspond to ×60, ×50 and ×40, respectively, the lens position of the original image is at $p_1$ and the magnification then is ×56, $C_B$=56/60≦0.933, $C_C$=56/50=1.12, $C_D$=56/40=1.4 are obtained. Moreover, this microcomputer 71 controls the above-described electronic zoom IC circuit 77 so as to perform electronic magnification of electronic magnifications $C_B$, $C_C$ and $C_D$ and in this way, three comparative observation depth images are formed under the same magnification as that of the original image.

Figure 8:
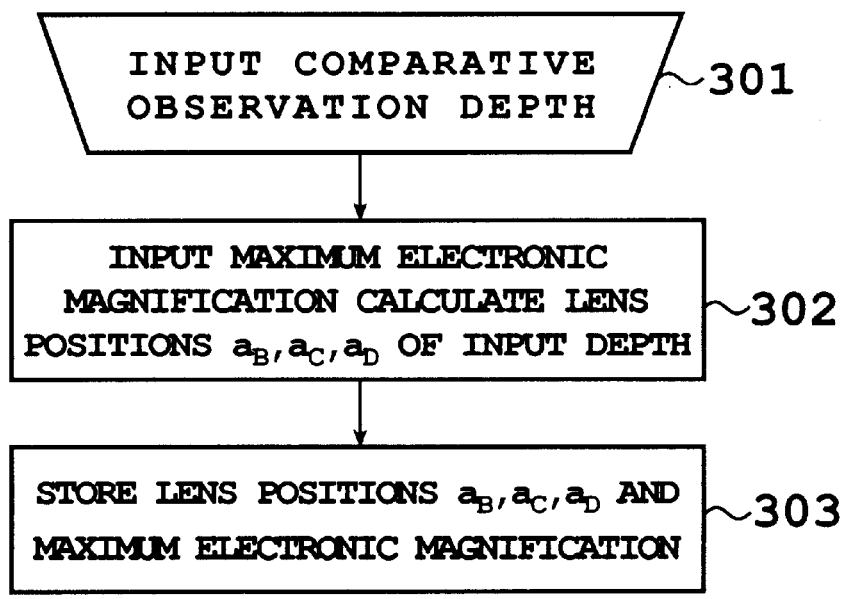
FIG. 8 is a flow chart showing a setting operation on different comparative observation depths according to the second embodiment.

The second embodiment is configured as shown above and its action will be explained below. FIG. 8 shows the setting of a comparative observation depth for a still image 4-screen display. In step 301, when depths of field 12 mm, 24 mm and 36 mm in FIG. 7 are entered from the function setting mode screen, etc. shown on the monitor 30 using the keys, etc. on the operation panel 85, the positions $a_B$, $a_C$ and $a_D$ of the movable lenses $L_2$ corresponding to these depths of field are calculated in step 302 and these lens positions are stored or retained in memory, etc. in the microcomputer 71 as the set values of the comparative observation depths in step 303. Furthermore, to prevent blurring of images by electronic magnification, a maximum magnification of allowable electronic magnification is also entered and stored.

Then, when the power scaling switch 67 of the operation section is operated when the electronic scope 60 is in use, an image in the Near direction magnified from the basic image and a reduced image in the Far direction returning to the basic image are obtained through control of movement of the second lens $L_2$ (and third lens $L_3$) as explained in FIGS. 2A and 2B and these images are taken by the CCD 12.

Then, the signal output from this CCD 12 is output through CDS/AGC circuit 24, DSP 26, electronic zoom IC circuit 77, etc., from the encoder 30 to the monitor 30 as in the case of the first embodiment and an optically magnified image of the object is displayed on this monitor 30. Furthermore, even if optical power scaling is finished, if a magnification operation of the power scaling switch 67 is performed, electronic magnification processing is performed at the same lens position (Near end) in FIG. 2B by the above-described electronic zoom IC circuit 77 and an optically magnified image of the object is further electronically magnified and displayed on the monitor 30.

Figure 9:
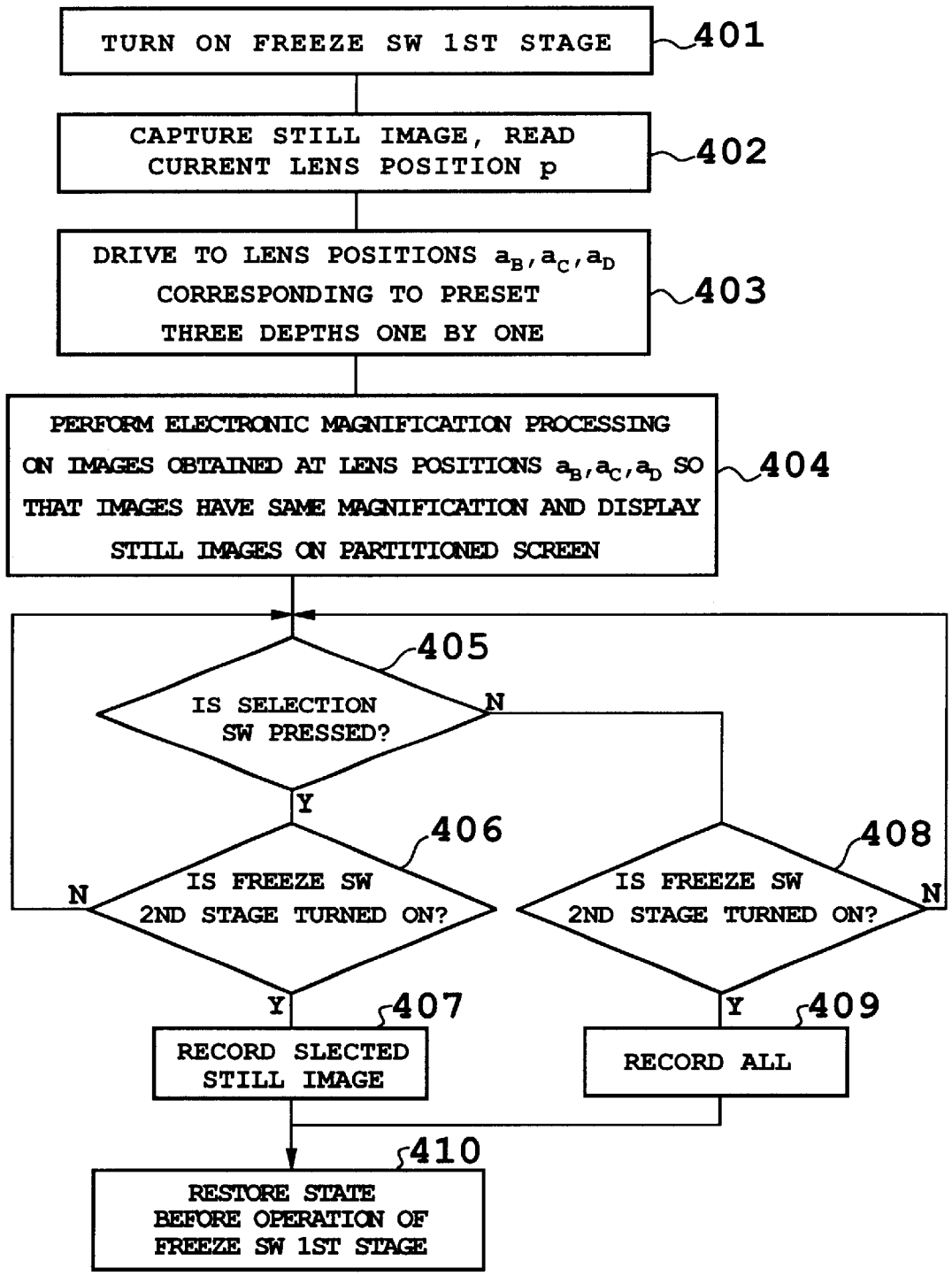
FIG. 9 is a flow chart showing an operation of a 4-partitioned screen display and recording of a still image according to the second embodiment.

FIG. 9 shows an operation of the still image during the above-described power scaling operation. When the first stage of the freeze switch (SW) 18 is turned ON in step 401, capturing of the still image is started in step 402 and the current position p of the second lens $L_2$ is read and the movable lens $L_2$ is driven from the current position to the lens positions of three comparative observation depths one by one in next step 403. That is, as explained in FIG. 7, the lens is driven to lens positions $a_B$, $a_C$ and $a_D$ corresponding to the depths of field of 12 mm (×60), 24 mm (×50) and 36 mm (×40), respectively.

Figure 10:
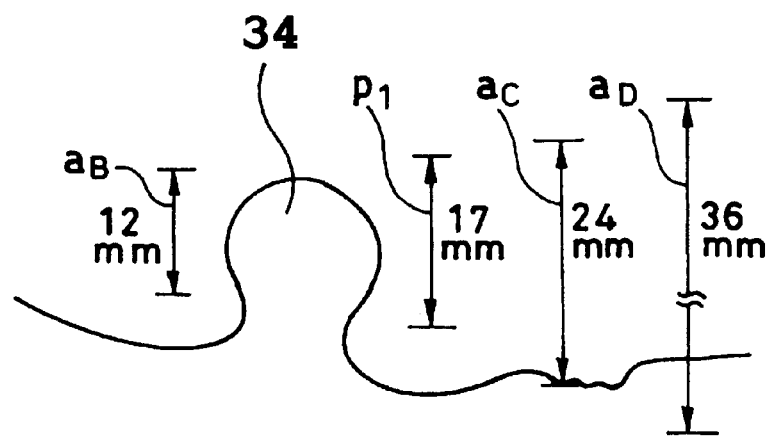
FIG. 10 illustrates different depths of field set with images of an object taken by the objective optical system according to the second embodiment.

FIG. 10 shows the depths of field of the object during such an operation. For example, the image of the object is sharply focused within a depth range of 17 mm at the lens position $p_1$ driven by the power scaling switch 67, focused within a depth range of 12 mm at the lens position $a_B$, focused within a depth range of 24 mm at the lens position $a_C$ and focused within a depth range of 36 mm at the lens position $a_D$.

In next step 404, magnifications $C_B$, $C_C$ and $C_D$ of electronic power scaling are calculated from the lens positions $a_B$ to $a_D$ of different comparative observation depths and the position $p_1$ of the second lens $L_2$ and electronic magnification processing is carried out based on this. That is, as explained in FIG. 7, assuming that the current lens position is $p_1$ (depth of field 17 mm, optical magnification ×56), $C_B$≦0.933, $C_C$=1.12, $C_D$=1.4. Therefore, in the electronic zoom IC circuit 77 in FIG. 6, the image obtained at the lens position $a_B$ is magnified by 0.933 times, the image obtained at the lens position $a_C$ is magnified by 1.12 times and the image obtained at the lens position $a_D$ is magnified by 1.4 times, and as a result, all four images including the original image become ×56 magnified still images. These four still images are stored in the image memory 28 temporarily and displayed on the 4-partitioned screen of the monitor 30.

Figure 11:
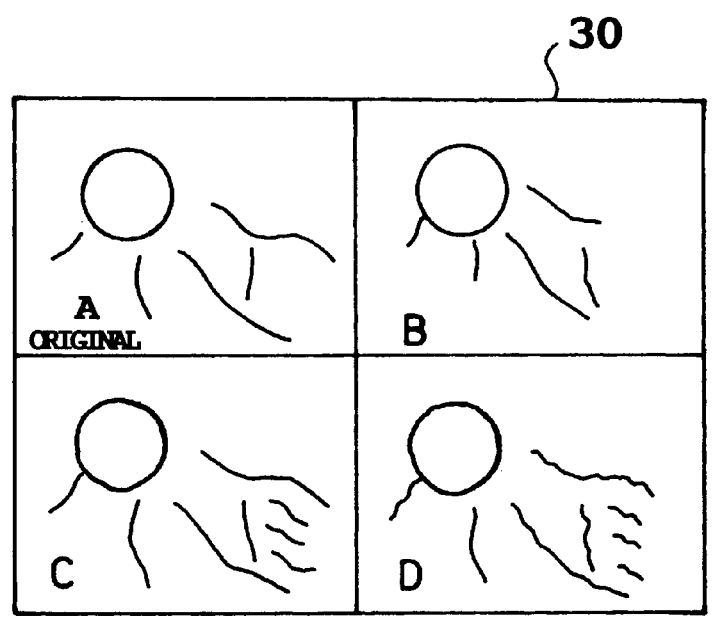
FIG. 11 illustrates a 4-partitioned screen display of a still image on a monitor according to the second embodiment.
Figure 12:
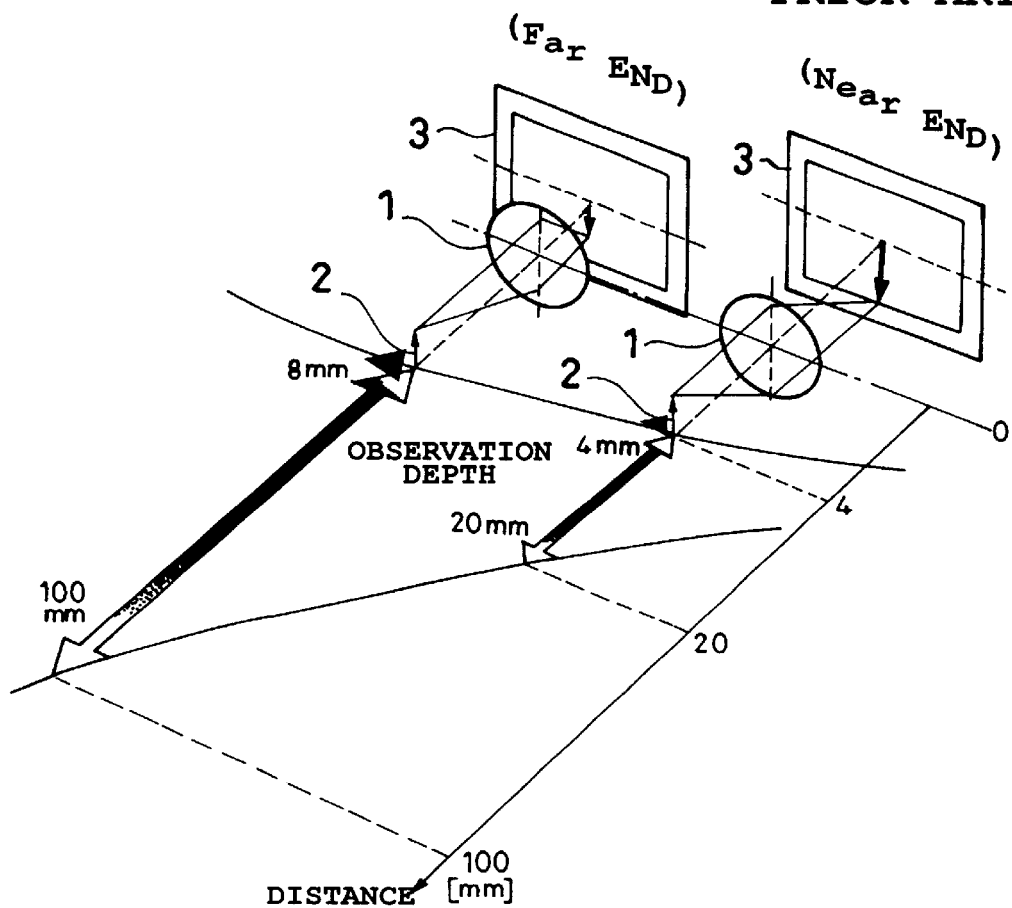
FIG. 12 illustrates a depth of field which is changed by an optical power scaling mechanism provided in an endoscope.
Figure 13:
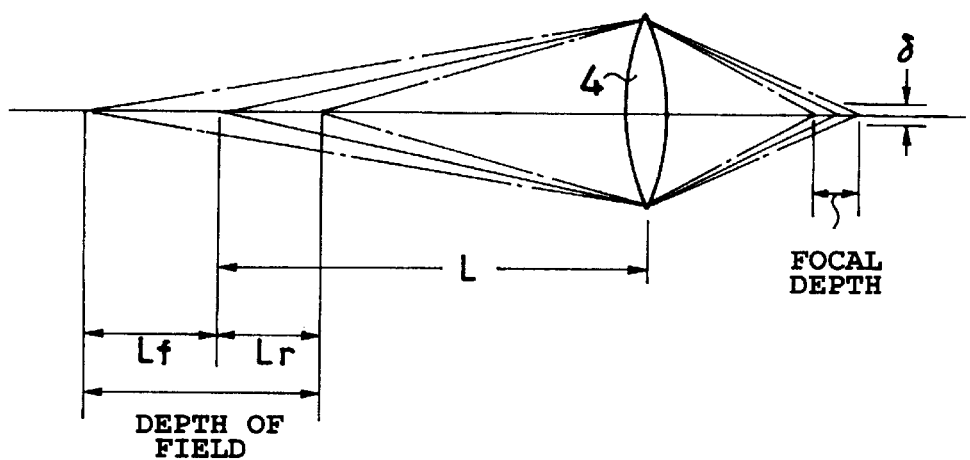
FIG. 13 illustrates a depth of field of a lens.

FIG. 11 shows a 4-partitioned screen display on the monitor 30 and this monitor shows the original image A, the image B obtained at a comparative observation depth of 12 mm (lens position $a_B$), the image C obtained at a comparative observation depth of 14 mm (lens position $a_C$) and the image D obtained at a depth of 28 mm (lens position $a_D$) on small screens of the 4-partitioned screen. These small screens also show information such as depths of field (optical magnification) and display magnification together.

Then, in step 405 of FIG. 9, it is decided whether the selection switch (SW) 86 is pressed or not. When Y (YES), it is decided whether the second stage of the freeze switch 68 is turned ON or not in step 406. When Y here, the still image selected by outputting a record trigger is recorded in a recording apparatus such as a hard copy in step 407. For example, when the still image C in FIG. 11 is selected by the selection switch 86 (button C), only this still image C is recorded. On the other hand, when N (NO) in step 405, it is decided in step 408 whether the second stage of the freeze switch 68 is turned ON or not, and when Y here, the process moves on to step 409 and all still images A to D are recorded in a recording apparatus such as a hard copy based on a recording trigger on the same 4-partitioned screen.

Then, in next step 410, processing of restoring the original condition before the operation of the first stage of the freeze switch 68 is carried out. That is, the second lens $L_2$ is returned to the position $p_1$ and at the same time electronic magnification processing to set the same magnification is stopped. By the way, the maximum value of electronic magnification is set to a predetermined value (×2, ×3) in the example and even if the above-described electronic magnifications $C_B$, $C_C$ and $C_D$ are equal to or greater than this value, magnification exceeding the predetermined value will be prevented, which prevents blurring of the image due to electronic magnification.

Thus, not only the still image A displayed by an operation of the power scaling switch 67 but also the still images B, C and D of different depths of field are displayed on the monitor 30 under the same magnification simultaneously, and therefore there is an advantage that it is possible to observe and record a still image sharply focused in the depth range to be observed.

In the above-described second embodiment, the operation of displaying still images of different depths of field on a 4-partitioned screen is limited to a power scaling operation. Furthermore, these operations can also be set to a still image 4-partitioned screen display mode and made selectively executable. Furthermore, it is also possible to perform 4-partitioned screen display not using the freeze switch 18 but using other switches.

Furthermore, comparative observation depths are set one by one in the above-described second embodiment, but it is also possible to set intervals of a plurality of comparative observation depths, for example, only 5 mm, and automatically set comparative observation depths at uniform intervals of 5 mm from the depths of field of that magnification (setting 24 mm, 29 mm or 34 mm for a power scaling operation of 17 mm in the case of FIG. 3) irrespective of the optical magnification at which the system is operating when the freeze switch 68 is operated and display these still images on the 4-partitioned screen.

As described above, the second embodiment includes the depth setting means for presetting comparative observation depths, drives and controls the objective optical system so that the above-described comparative observation depth is set when a predetermined operation is carried out during execution of optical power scaling, and at the same time electronically scales power so that the magnification of the image with the comparative observation depth captured by the image pickup element becomes the same as the magnification immediately before the above-described predetermined operation, and can thereby display a plurality of magnified images of an object captured during an optical power scaling operation of different depths of field and of the same magnification on a partitioned screen, etc. and obtain still images, etc. with blurring in the depth direction eliminated.

What is claimed is:

1. An electronic endoscope having a power scaling function comprising:
    an objective optical system that optically scales an image under observation using power scaling lenses;
    an electronic power scaling circuit that electronically scales an image obtained through an image pickup element through signal processing;
    depth operating means for changing the depth of field in optical power scaling of said objective optical system to an arbitrary value; and
    a control circuit that drives and controls said objective optical system so that the depth of field selected through the operation of this depth operating means is obtained and controls the electronic power scaling operation of said electronic power scaling circuit so that the image magnification immediately before said operation is maintained.

2. The electronic endoscope having a power scaling function according to claim 1, wherein when the depth of field is changed to an arbitrary value, said control circuit controls so that electronic power scaling exceeding a preset allowable magnification is not performed.

3. The electronic endoscope having a power scaling function according to claim 1, wherein said depth operating means comprises a selection switch that selects a plurality of preset depth of field values and a variable switch to change the depth of field value selectable using this switch.

4. The electronic endoscope having a power scaling function according to claim 1, wherein when an operation of changing the depth of field is performed, said depth operating means deepens the depth of field by a predetermined amount from the immediately preceding value.

5. An electronic endoscope having a power scaling function comprising:
    an objective optical system that optically scales an image under observation using power scaling lenses;
    an electronic power scaling circuit that electronically scales an image obtained through an image pickup element through signal processing;
    depth setting means for presetting a comparative observation depth of the depth of field that varies by said optical power scaling operation; and
    a control circuit that drives and controls said objective optical system so that the comparative observation depth set by said depth setting means is obtained when a predetermined operation is performed during execution of optical power scaling and at the same time controls the electronic power scaling operation of said electronic power scaling circuit so that the image magnification of said comparative observation depth taken by said image pickup element becomes the same as the magnification immediately before said predetermined operation.

6. The electronic endoscope having a power scaling function according to claim 1, wherein said predetermined operation is a still image display operation by a freeze switch and the still image during a freeze switch operation and the still image of said comparative observation depth are displayed on a partitioned screen on the monitor simultaneously.

7. The electronic endoscope having a power scaling function according to claim 1, wherein said depth setting means presets a plurality of comparative observation depth values and when a freeze switch operation is performed, a plurality of still images of different comparative observation depths is displayed on a partitioned screen on the monitor.

8. The electronic endoscope having a power scaling function according to claim 1, wherein said depth setting means automatically sets a plurality of comparative observation depths at predetermined intervals.

* * * * *